(12) United States Patent
Seo et al.

(10) Patent No.: US 6,599,519 B1
(45) Date of Patent: Jul. 29, 2003

(54) BIODEGRADABLE POLY(ALKYLENE OXIDE)-POLY(P-DIOXANONE) BLOCK COPOLYMER SOLUBLE IN ORGANIC SOLVENTS, AND DRUG DELIVERY COMPOSITION COMPRISING SAME

(75) Inventors: Min-Hyo Seo, Daejeon (KR); In-Ja Choi, Daejeon (KR)

(73) Assignee: Samyang Corporation (KR)

( * ) Notice: Subject to any disclaimer, the term of this patent is extended or adjusted under 35 U.S.C. 154(b) by 0 days.

(21) Appl. No.: 09/763,921

(22) PCT Filed: Jul. 18, 2000

(86) PCT No.: PCT/KR00/00779

§ 371 (c)(1),
(2), (4) Date: Jun. 28, 2001

(87) PCT Pub. No.: WO01/05379

PCT Pub. Date: Jan. 25, 2001

(51) Int. Cl.$^7$ .............................. A61K 9/00; A61K 9/48; A61K 39/00; A61K 9/14; A61F 2/00

(52) U.S. Cl. ...................... 424/426; 424/400; 424/402; 424/451; 424/184.1; 424/422; 424/423; 424/489; 424/486; 424/487; 424/484

(58) Field of Search ................. 424/426, 400, 424/402, 451, 184.1, 422, 423, 489, 486, 487, 484; 606/230; 525/408, 409, 411, 413, 415; 528/354, 421; 514/44, 169, 54.07, 254, 9

(56) References Cited

U.S. PATENT DOCUMENTS 5,019,094 A * 5/1991 Brezwada et al. .......... 606/230
5,522,841 A * 6/1996 Roby et al. ................. 606/230

* cited by examiner

Primary Examiner—James M. Spear
Assistant Examiner—Blessing Fubara
(74) Attorney, Agent, or Firm—Thorpe North & Western, LLP

(57) ABSTRACT

The present invention relates to a biocompatible and biodegradable block copolymer of poly(alkylene oxide) and poly (p-dioxanone), which is soluble in organic solvents, and a drug delivery composition comprising the same.

16 Claims, No Drawings

BIODEGRADABLE POLY(ALKYLENE OXIDE)-POLY(P-DIOXANONE) BLOCK COPOLYMER SOLUBLE IN ORGANIC SOLVENTS, AND DRUG DELIVERY COMPOSITION COMPRISING SAME

This application is a 371 of PCT/KR00/00779 filed Jul. 18, 2000.

TECHNICAL FIELD

The present invention relates to a biocompatible and biodegradable block copolymer of poly(alkylene oxide) and poly(p-dioxanone) which is soluble in organic solvents. More particularly, the invention relates to a composition comprising the block copolymer for delivering bioactive agents and methods of use thereof.

BACKGROUND ART

The concept of using polymers for the controlled release of active drugs and other therapeutic compounds in medical applications has emerged and been developed extensively in the last two decades. When polymers are used for the delivery of pharmacologically active agents in vivo, it is essential that the polymers themselves be nontoxic and degrade into non-toxic products as the polymer is eroded by the body fluids. Many synthetic biodegradable polymers, however, upon erosion in vivo yield oligomers and monomers that adversely interact with the surrounding tissue. To minimize the toxicity of the intact polymer carrier and its degradation products, polymers have been designed based on naturally occurring metabolites.

Poly(lactic acid)(PLA), poly(glycolic acid)(PGA), and copolymers thereof, have been used as drug carriers in the form of microspheres, nanospheres, implants and fibers. These polymers are polyesters that, upon implantation in the body, undergo simple hydrolysis. The products of such hydrolysis are biologically compatible and metabolizable moieties (i.e. lactic acid and glycolic acid), which are eventually removed from the body by the citric acid cycle. Drug release from these polymers occurs by two mechanisms. First, diffusion results in the release of drug molecules from the implant surface. Second, subsequent release occurs by the cleavage of the polymer backbone, defined as bulk erosion. Several implant studies have proven these polymers safe in drug delivery applications when used in the form of matrices, microspheres, bone implant materials, surgical sutures, and also as long term contraceptives. Thus, these polymers have been time-tested in various applications and proven safe for human use. Most importantly, these polymers are FDA-approved for human use.

However, these polymers do have drawbacks. For example, due to their strong hydrophobicity they undergo hydrolysis slowly in vivo which may cause an undesirably slow rate of drug release. When the drug to be delivered is a high molecule weight protein drug, the activity of the protein drug is significantly lowered due to the relatively long binding duration of the protein drug to the hydrophobic polymer. In order to solve such problems a number of studies have been conducted to impart a suitable degree of hydrophilicity to the predominantly hydrophobic PLA, PGA or other hydrophobic biodegradable polymers by way of introducing hydrophilic polymer moieties therein. In these studies, block copolymers of PLA, PGA or other biodegradable polymers containing bicompatible poly(ethylene oxide) in the form of a hydrophilic polymer block, have been developed to obtain an improved drug delivery polymer composition (see U.S. Pat. Nos. 4,862,168, 4,452,973, 4,716,203, 5,683,723, 4,942,035, 5,384,333, 5,476,909, 5,548,035, 5,702,717, 5,449,513, 5,510,103, and 5,543,158)

Doddi et al. (U.S. Pat. No. 4,052,988) have reported that poly(p-dioxanone), a polymer of 1,4-dioxane-2-one, is a new class of biodegradable polymer which has superior properties over other existing biodegradble polymers that are used for the purpose of preparing surgical sutures. To further improve the rheological properties of poly (dioxanone) for suture applications there have also been developed poly(p-dioxanone) copolymers (see U.S. Pat. Nos. 4,643,191, 5,080,665, and 5,019,094).

However, the above-mentioned homopolymers and copolymers of p-dioxanone are not soluble in common organic solvents which renders them not suitable to be used as biocompatible/biodegradable drug carriers.

DISCLOSURE OF THE INVENTION

The present invention provides a biocompatible and biodegradable block copolymer of p-dioxanone and alkylene oxide, which is soluble in common organic solvents and is suitable for use as a drug delivery carrier.

The present invention also provides a composition and a formulation for drug delivery comprising said block copolymer.

The block copolymer of the present invention, which is soluble in pharmaceutically acceptable solvents, comprises one or more poly(alkylene oxide) blocks and one or more blocks of a p-dioxanone homopolymer or copolymer, wherein the amount of the poly(alkylene oxide) blocks is within a range of 25 to 85% by weight, based on the total amount of the block copolymer.

Before the present block compolymer composition and method of use in delivery of a bioactive agent are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular form "a," "an," and "the" include plural referents unless the context clearly dictates otherwise. Thus, for example, reference to a polymer containing a "block" includes reference to two or more of such blocks, and reference to "a drug" includes reference to two or more of such drugs.

As used herein, the term "drug" or "bioactive agent" or any other similar term means any chemical or biological material or compound suitable for administration by methods previously known in the art and/or by the methods taught in the present invention and that induce a desired biological or pharmacological effect, which may include but is not limited to (1) having a prophylactic effect on the organism by preventing an undesired biological effect, such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anaesthetic effect, or it may be systemic. This invention is not drawn to novel drugs or to new classes of bioactive agents. Rather it is limited to the compositions and methods of delivery of agents that exist in the state of the art or that may later be established as active agents and that are suitable for delivery by the present invention. Such substances include broad classes of compounds normally delivered into the body. In general, this includes but is not limited to antiinfective such as antibiotics and antiviral agents; analgesics and analgesic combinations; anorexics; antihelminthics; antiarthritics; antiasthmatic agnets; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral, central nervous system stimulants-;vasoconstrictors; cough and cold preparations, including decongestants; hormones such as estradiol and other steroids, including corticosteriods, hypnotics, immunosuppressive, muscle relaxants; parasympatholytics, psychostimulants; sedatives; and tranquilizers. By the method of the present invention, both ionized and nonionized drugs may be delivered, as can drugs of either high or low molecular weight. Also included in the scope of these terms are nucleic acids, such as DNA, RNA, and oligonucleotides.

As used herein "effective amount" means an amount of a drug or bioactive agent that is nontoxic but sufficient to provide the desired local or systemic effect and performance at a reasonable benefit/risk ratio that would attend any medical treatment.

As used herein "peptide" means a peptide of any length and includes proteins. The terms "polypeptide" and "oligopeptide" are used herein without any particular intended size limitation, unless a particular size is otherwise specified. Typical of peptides that can be utilized are those selected from the group consisting of oxytocin, vasopressin, adrenocorticotrophic hormone, epidermal growth factor, prolactin, luliberin or luteinising hormine releasing hormone, growth hormone, growth hormone releasing factor, insulin, somatostatin glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, "administering" and similar terms mean delivering the composition to the individual being treated such that the composition is capable of being circulated sytemically to the parts of the body where the composition binds to the target cells and is taken up by endocytosis. Thus, the composition is preferably administered systematically to the individual, typically by subcutaneous, intramuscular, or intravenous means, or by intraperitoneal administration. Injectables for such use can be prepared in conventional forms, either as a liquid solution or suspension or in a solid form that is suitable for preparation as a solution or suspension in a liquid prior to injection, or as an emulsion. Suitable excipients include, for example, water, saline, dextrose, glycerol, ethanol, and the like, and if desired, minor amounts of auxiliary substances such as wetting or emulsifying agent, buffers, and the like can be added.

The block copolymer of the present invention is composed of at least one hydrophilic block of poly(alkylene oxide) and at least one hydrophobic block of a p-dioxanone homopolymer or copolymer. The block copolymer of the present invention is biocompatible, biodegradable and dissolves readily in solvents that are commonly used in the preparation of polymeric drug compositions. Therefore, it can be effectively employed as a carrier for delivering a drug.

Specifically, the block copolymer according to the present invention may be represented by formulas (I), (II), (III) or (IV):

    RO—A—B—OH    (I)

    RO—B—A—B—OR    (II)

    RO—A—B—A—OR    (III)

    RO—(A—B)$_n$—OR    (IV)

Wherein R is hydrogen, an alkyl or acyl group having 1~20 carbon atoms; n is an integer of 2 to 100; A represent a hydrophillic block selected from the group consisting of poly(alkylene oxide), such as poly(ethylene oxide), and copolymers and block copolymers of ethylene oxide and propylene oxide; and B represents a hydrophobic block selected from the group consisting of poly(p-dioxanone), a block or random copolymer of 1,4-dioxanone and at least one comonomer selected from the group consisting of lactic acid, glycolic acid and carprolactone.

In accordance with the present invention, the content of the combined hydrophilic polymer A block may range from 25 to 80% by weight, preferably from 30 to 70% by weight, of the block copolymer. When the content of the A block is below 25% by weight, the block copolymer is not soluble in solvents commonly used in making a biodegradable polymer solution, and when the content of the A block exceeds 80% by weight of the block copolymer, the block copolymer may not function as a drug delivery carrier because of its excessive water solubility.

The content of the A block is preferably controlled in such a way that the block copolymer has a water-solubility of less than 1.5 g/ml (at 25° C.). Representative examples of the hydrophilic polymer A block include various forms of poly(alkylene oxides), preferably, a water-soluble poly (ethylene oxide), a water-soluble copolymer of ethylene oxide and propylene oxide and monoalkoxy-ended derivatives thereof. Preferably the monoalkoxy-terminated derivatives are (I), (II), (III) or (IV) and the derivatives disclosed in examples 1–7, the average molecular weight of the A blocks of the copolymer is within a range of 200 to 500,000 Daltons, more preferably 2,000 to 50,000 Daltons, and most preferably 2,000 to 20,000 daltons. When a water-soluble ethylene-propylene copolymer is used as the A block, the ethylene content of the ethylene-propylene copolymer is preferably 50 mol % or more.

Suitable hydrophobic polymer B blocks of the block copolymer of the present invention include poly(p-dioxanone) and may be selected from the group consisting of a homopolymer of 1,4-dioxane-2-one and a block or random copolymer of 1,4-dioxane-2-one and at least one monomer selected from the group consisting of lactic acid, glycolic acid and caprolactone. The hydrophobic B block can be hydrolysed by water, assisted by an enzyme in vivo, and thus it functions to control the degradation rate of the block copolymer. In the case of using a dioxanone copolymer as the B block, the hydrophobicity and the hydrolysis rate of the block copolymer may be controlled by adjusting the content of the comonomer such as lactic acid, glycolic acid or caprolactone. Specifically, the rate of degradation of the hydrophobic block decreases as the content of lactic acid or caprolactone increases, whereas it increases as the glycolic acid content increases. Accordingly, the block copolymer of the present invention comprising such hydrophobic copolymer provides a drug delivery carrier by which a controller release of the drug can be effectively achieved.

Preferably, the average molecular weight of the hydrophobic B blocks of the copolymer of the present invention is within a range of 500 to 100,000 Daltons, more preferably 500 to 50,000 Daltons and most preferably from 1,000 to 50,000 Daltons. When a copolymer of 1,4-dioxane-2-one and lactic acid, glycolic acid or caprolactone is used as the B block, the 1,4-dioxane-2 one content is preferably at least 5 mol %, and more preferably is within a range of 30 to 70 mol %, based on the total amount of monomer used in the preparation of said copolymer.

PLA, PGA and copolymers thereof have been used as the hydrophobic component of the block used in preparing a drug delivery carrier. However, due to their high glass transition temperature (Tg) of about 45 to 65° C. and a high modulus of about 2.0 Gpa, they have poor processability in the fabrication of a drug delivering carrier. Furthermore, since these polymers are amorphous, they cannot be processed into the form of a powder if their molecular weight is less than 3,000 Daltons.

In contrast, since the poly)p-dioxanone) derivative employed as the hydrophobic polymer B block in the present invention has relatively low Tg of about 10° C. a relatively low modulus of about 1.5 Gpa and a crystallinity of about 55%, it enables the block copolymer to maintain a stable solid form even if its molecular weight is less than 3,000 Daltons. In the present invention, it is preferred to employ a poly(p-dioxanone) due to its relatively high crystallinity.

As represented by formulas (I) to (IV), the present invention provides a block copolymer of a hydrophilic A and a hydrophobic B polymer wherein the A–B blocks may be linked by an ester, amide or urethane linkage, and both the hydrophilic and hydrophobic blocks are readily degradable in vivo in an aqueous environment with the aid of an enzyme. The present block copolymer has the significant advantage in that it can be dissolved in solvents commonly used in preparing biodegradable polymer solutions. Representative examples of solvents include methylene chloride, chloroform, ethanol, methanol, isopropanol, butanol, acetic acid, formic acid, ethyl acetate, methyl acetate, acetonitrile, acetone, 1,4-dioxane, N,N-dimethyl formamide, N,N-dimethyl acetamide, dimethyl sulfoxide, N-methylpyrolidone, of a mixture thereof. The preferred solvent for the present invention is a member selected from the group consisting of methylene chloride, ethanol, ethyl acetate, acetonitrile, N,N-dimethyl formamide, N-methylpyrrolidone, and a mixture thereof.

The block copolymers of the present invention may be synthesized as follows. In the presence of both a metal catalyst and a poly(alkylene oxide), 1,4-dioxane-2-one undergoes a ring-opening polymerization reaction, alone or together with lactide, glycolide or caprolactone to give a copolymer of formulas (I) or (II), depending on whether one end of the poly(alkylene oxide) is alkoxy-ended or hydroxy-ended. The reaction is preferably carried out without an added solvent at a temperature ranging from 70 to 160° C., preferably from 80 to 130° C. for 3 to 24 hours. Exemplary catalysts that may be used in the above reaction include stannous octate, tributyl aluminum, triethyl aluminum, zinc carbonate, zinc chloride and titanium chloride, preferably stannous octate.

The synthesized block copolymer may be purified by dissolving the crude product in an organic solvent, e.g., dichloromethane or chloroform, followed by adding the resulting solution to an organic solvent, e.g., methanol or dimethyl ether, which dissolves the 1,4-dioxane-2-one monomer but not the copolymer, to precipitate the desired copolymer. The structure and molecular weight of a purified copolymer may be determined by H-NMR (nuclear magnetic resonance). FT-IR and GPC (gel permeation chromatography).

The block copolymers of formulas (III) or (IV), according to the present invention, may be synthesized by using the copolymers of formulas (I) and (II) in accordance with the coupling reactions (1) and (2), respectively.

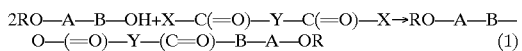

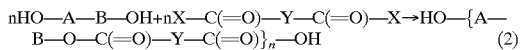

Wherein X is HO, Cl, or Br, Y is —(CH$_2$)m— or —C$_6$H$_4$, m is an integer of 0 to 12, and n is as defined previously.

The linkers that can be used in the above coupling reactions, include those having two reactive groups in the molecule and are preferably biocompatible compounds which can be metabolized in vivo, i.e. an organic acid selected from the group consisting of oxalic acid, malonic acid, succinic acid, glutaric acid, adipic acid, phthalic acid, and the chloride and bromide salts thereof. When an organic acid is used, it is desirable to employ a suitable dehydrating agent such as dicyclo carbodiimide, oxalic acid chloride, thionyl chloride or triphenyl phosphine to promote the coupling reaction.

The block copolymers of formulas (III) and (IV) of the present invention may also be synthesized by using a diisocyanide derivative in accordance with the urethane coupling reactions (3) and (4), respectively:

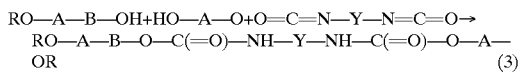

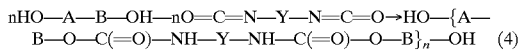

Wherein Y and n are as defined previously.

Since the poly(p-dioxanone)-poly(alkylene oxide) block copolymer of the present invention is dissolvable in either an organic solvent or aqueous organic solvent, it is possible to convert the block copolymer of the present invention into one of the following forms: a microsphere, microcapsule, nanosphere, nanocapsule, polymer micelle, strip, film stick, fiber, gel, sol and the like, and be used as drug delivery carriers.

The A—B type diblock copolymer of the present invention is useful in the preparation of a nanosphere or polymer micelle carrying a poorly soluble drug, which may be injected intravenously, for sustained release of the drug in the blood. The nanosphere or polymer micelle composition preferably has a particle size ranging from 10 to 600 nm, and more preferably from 10 to 300 nm. Examples of poorly soluble drugs include anti-cancer drugs such as paclitaxel, cisplatin, caboplatin, doxorubicin, camtotecin, 5-fluorouracil, cytosine, arabinose, methotrexate, antiphlogistic anodynes such as indomethacin, probiprofen, ketoprofen, piroxicam, diclofenac, and antibiotics such as cyclosporine, etraconazole, ketoconazole, tetracycline, minocycline, doxycycline, ofloxacin, ciprofloxacin, gentamicin, amphotericin B and the like.

The A—B—A or B—A—B type triblock copolymer and the (A—B)$_n$ type multiblock copolymer may used in the preparation of a drug composition in the form of a microsphere, microcapsule, film, strip, implant formulation, polymer gel or sol containing a physiologically active ingredient prepared by conventional methods, e.g., solvent evaporation, spray dry or solvent extraction. A formulation prepared from the above composition may be injected or implanted into subcutaneous tissue or muscle for the sustained release of the physiologically active ingredient. Suitable physiologically active ingredients include peptide or protein drugs, anti-cancer drugs, antiphlogistic anodynes, antibiotics, growth hormones such as human growth hormone, procine growth hormone, bovine growth hormone and the like; growth factors such as leukocyte promoting factors, erythrocyte prompting drugs, osteogenetic proteins, platelet sensitive agents, epithelial cell growth factors, brain growth factors and the like, LH—RH agonist such as leuprorelin acetate goserelin acetate and the like, other peptides such as insulin, glucagons, octreotide, calcitonin, decapeptyl, follicle-stimulating hormone, interferon and the like, sex hormones such as testosterone, progesterone, estradiol, estrogen and the like, vaccines, and genes.

BEST MODE FOR CARRYING OUT THE INVENTION

The following Examples and Comparative Examples are provided for purposes of illustrating certain aspects of the present invention only and they are not to be construed as limiting the scope of the present invention in any way.

EXAMPLE 1

This example illustrates the preparation of a mPEG-PDO [poly(p-dioxanone)] diblock copolymer according to formula I.

5 g (0.025 mmole) of poly(ethylene glycol) monomethyl ether (Mw mPEG 2,000 daltons) was added in a 2-necked 100 ml round-bottomed flask and dried in a dry nitrogen atmosphere under reduced pressure (1 mmHg) at 100° C. for 3 hours. Using a syringe, 10.3 mg of stannous octoate in toluene, which is an amount corresponding to 1.0 mol % of poly(ethylene glycol) monomethyl ether was added into the flask. The resulting mixture was stirred for 30 minutes and toluene was removed at 110° C. under a reduced pressure(1 mmHg). To this was added 5 g of purified 1,4-dioxane-2-one and the mixture was allowed to react at 80° C. for 24 hours.

The polymer thus obtained was dissolved in dichloromethane, and diethyl ether was added thereto, with stirring, to induce preparation of the polymer. The precipitated polymer was dried in a vacuum oven for 48 hours in order to obtain an mPEG-PDO diblock copolymer(Mw 2,000–1,180 Daltons), where the poly(p-dioxanone) (PDO) block had an average molecular weight of 1,180 Daltons and the mPEG content of this copolymer was 62.9 wt %.

EXAMPLE 2

This example illustrates the preparation of a mPEG-PDO diblock copolymer according to formula I.

The procedure of Example 1 was repeated using 5 g of poly(ethylene glycol) monomethyl ether(Mw 2,000 Daltons). 7.5 g of 1,4-dioxane-2-one and 10.13 mg of stannous octate to obtain an mPEG-PDO diblock copolymer (Mw 2,000–1,620 Daltons). The mPEG content of this copolymer was 55.2 wt %.

EXAMPLE 3

This example illustrates the preparation of a mPEG-PDO diblock copolymer according to formula I.

The procedure of Example 1 was repeated using 5 g of poly(ethylene glycol) monoethyl ether(Mw 2,000 Daltons), 10 g of 1,4-dioxane-2-one and 10.13 mg of stannous octoate to obtain a mPEG-PDO diblock copolymer(Mw 2,000–2,100 Daltons). The mPEG content of this copolymer was 48.8 wt %.

EXAMPLE 4

This example illustrates the preparation of a mPEG-PDO diblock copolymer according to formula I.

The procedure of Example 1 was repeated using 5 g of poly(ethylene glycol) monomethyl ether(Mw 5,000 Daltons), 10 g of 1,4-dioxane-2-one and 4.06 mg of stannous octoate to obtain a mPEG-PDO diblock copolymer(Mw 5,000–5,800 Daltons). The mPEG content of this copolymer was 46.3 wt %.

EXAMPLE 5

This example illustrates the preparation of a mPEG-PDO diblock copolymer according to formula I.

The procedure of Example 1 was repeated using 5 g for poly(ethylene glycol) monomethyl ether(Mw 12,000 Daltons), 10 g of 1,4-dioxane-2-one and 1.70 mg of stannous octoate to obtain a mPEG-PDO diblock copolymer(Mw 12,000–13,200 Daltons). The mPEG content of this copolymer was 47.6 wt %.

EXAMPLE 6

This example illustrates the preparation of a mPEG—PDO/PLA diblock random copolymer according to formula I.

The procedure of Example 1 was repeated using 5 g of poly(ethylene glycol) monomethyl ether (Mw 2,000 Daltons), 2.07 g of 1,4-dioxane-2-one and 2.93 g of lactic acid and 1.70 mg of stannous octoate at a reaction temperature of 110° C. to obtain a mPEG-PDO/PLA diblock copolymer(Mw 2,000–710/1,120 Daltons). The mPEG content of this copolymer was 52.2 wt %.

EXAMPLE 7

This example illustrates the preparation of a mPEG-PDO/PLA diblock random copolymer according to formula I.

The procedure of Example 1 was repeated using 5 g of poly(ethylene glycol) monomethyl ether(Mw 5,000 Dalton), 2.07 g of 1,4-dioxane-2-one and 2.93 g of lactic acid and 10.13 mg of stannous octoate at a reaction temperature of 110° C. to obtain a mPEG-PDO/PLA diblock copolymer (Mw 5,000–1750/2,620 Daltons). The mPEG content of this copolymer was 53.4 wt %.

EXAMPLE 8

This example illustrates the preparation of a PDO-PEG-PDO triblock copolymer according to formula II.

The procedure of Example 1 was repeated using 10 g of poly(ethylene glycol) (Mw 1,000 Daltons), 20 g of 1,4-dioxane-2-one and 81.0 mg of stannous octoate to obtain a PDO-PEG-PDO triblock copolymer (Mw 580–1,000 Daltons). The PEG contents of this copolymer was 46.3 wt %.

EXAMPLE 9

This example illustrates the preparation of a PDO-PEG-PDO triblock copolymer according to formula II.

The procedure of Example 1 was repeated using 10 g of poly(ethylene glycol) (Mw 3,400 Daltons), 40 g of 1,4-dioxane-2-one and 23.8 mg of stannous octoate to obtain a PDO-PEG-PDO triblock copolymer (Mw 3,640–3,400–3,640 Daltons). The PEG content of this copolymer was 31.8 wt %.

EXAMPLE 10

This example illustrates the preparation of a PDO-PEG-PDO triblock copolymer according to formula II.

The procedure of Example 1 was repeated using 10 g of poly(ethylene glycol) (Mw 1,200 Daltons), 40 g of 1,4-dioxane-2-one and 6.75 mg of stannous octoate to obtain a PDO-PEG-PDO triblock copolymer (Mw 12,600–12,000–12,600 Daltons). The PEG content

EXAMPLE 11

This example illustrates the preparation of a PDO/PLA-PEG-PDO/PLA triblock copolymer according to formula II.

The procedure of Example 1 was repeated using 10 g of poly(ethylene glycol) (Mw 3,400 Daltons), 8.29 g of 1,4-dioxane-2-one, 11.71 g of lactic acid and 23.83 mg of stannous octoate to obtain a PDO/PLA-PEG-PDO/PLA triblock copolymer (Mw 1,290/1,710–3,400–1,290/1,710 Daltons). The PEG content of this copolymer was 36.2 wt %.

EXAMPLE 12

This example illustrates the preparation of a PDO/PLA-PEG-PDO/PLA triblock copolymer according to formula II.

The procedure of Example 1 was repeated using 10 g of poly(ethylene glycol) (Mw 3,400 Daltons), 12.46 g of 1,4 dioxane-2-one, 7.54 g of lactic acid and 23.83 may of stannous octoate to obtain a PDO/PLA-PEG-PDO/PLA triblock copolymer(Mw 2,410/841–3,400–2,410/841 Daltons. The PEG content of this copolymer was 34.3 wt %.

EXAMPLE 13

This example illustrates the preparation of a mPEG-PDO-mPEG triblock copolymer according to formula III.

11.2 g(3.5 mmole) of the mPEG-PDO-OH(Mw 2,000–1,180 Daltons) diblock copolymer synthesized in Example 1 and 0.4 g(4 mmole) of succinic acid chloride were added to 50 ml of absolute toluene in a container. Then, 1 ml of pyridine was added to the container and the mixture was stirred at 120° C. for 12 hours. Toluene was removed by evaporation and the resulting product was dissolved in dichloromethane followed by filtration to remove the solid precipitates. The supernatant was added to diethyl ether, and the precipitated polymer was filtered and dried in vacuum for 24 hours to obtain 9.85 g of an mPEG-PDO-mPEG triblock copolymer (yield (82.08%). The completion of the reaction was confirmed by FT-IR which showed complete disappearance of the O—H vibration absorption band at 3,200–3,500 cm$^{-1}$. The mPEG content of this copolymer was 62.9 wt % and the average molecular weight of the copolymer is 6,360 Daltons.

EXAMPLE 14

This example illustrates the preparation of a mPEG-PDO/PLA-mPEG triblock copolymer according to formula III.

The procedure of Example 13 was repeated using 10 g(0.26 mmole) of the mPEG-PDO/PLA-OH diblock copolymer synthesized in Example 6 and 0.356 g(0.26 mmole) of 1,6-diisocyanohexane, to obtain a mPEG-PDO/PLA-mPEG triblock copolymer (yield 88.8%). The mPEG content of this copolymer was 52.2 wt % and the average molecular weight of the copolymer is 7,660.

EXAMPLE 15

This example illustrates the preparation of a (PDO-PEG)$_n$ multiblock copolymer according to formula IV.

The procedure of Example 13 was repeated using 10 g of the HO-PDO-PEG-PDO-OH triblock copolymer synthesized in Example 8 and 0.72 g(4.6 mmole) of succinic acid chloride, to obtain 9.54 g of a (PDO-PEG)$_n$ multiblock copolymer(yield 90.0%, Mw 24,000 Daltons). The PEG content of this copolymer was 46.3 wt %.

EXAMPLE 16

This example illustrates the preparation of a mPEG-PDO/PLA diblock copolymer according to formula I.

The procedure of Example 1 was repeated using 5 g of poly(ethylene glycol) monomethyl ether(Mw 5,000 Daltons), 1 g of 1,4-dioxane-2-one, 1.5 g of lactic acid and 10.13 mg of stannous octoate at a reaction temperature of 110° C. to obtain a mPEG-PDO/PLA diblock copolymer (Mw 5,000–780/1,210 Daltons). The mPEG content of this copolymer was 71.5 wt %.

EXAMPLE 17

This example illustrates the preparation of a PDO-PEG-PDO triblock copolymer according to formula II.

The procedure of Example 1 was repeated using 10 g of poly(ethylene glycol) (Mw 3,400 Daltons), 8 g of 1,4-dioxane-2-one and 23.8 mg of stannous octoate at a reaction temperature of 80° C. to obtain a PDO-PEG-PDO (Mw 720–3,400–720 Daltons). The PEG content of this copolymer was 70.2 wt %.

EXAMPLE 18

This example illustrates the preparation of a mPEG-PDO diblock copolymer according to formula I.

The procedure of Example 1 was repeated using 5 g of poly(ethylene glycol) monomethyl ether(Mw 2,000 Daltons), 40 g of 1,4-dioxane-2-one and 10.13 mg of stannous octoate at a reaction temperature of 80° C. to obtain a mPEG-PDO diblock copolymer(Mw 2,000–9,520 Daltons). The mPEG content of this copolymer was 17.4 wt %.

EXAMPLE 19

This example illustrates the preparation of a PDO-PEG-PDO triblock copolymer according to formula II.

The procedure of Example 1 was repeated using 5 g of poly(ethylene glycol)(Mw 1,000 Daltons), 35 g of 1,4-dioxane-2-one and 40.5 mg of stannous octoate at a reaction temperature of 100° C. to obtain a PDO-PEG-PDO triblock copolymer (Mw 2,100–1,000–2,100 Daltons). The PEG content of this copolymer was 19.2 wt %.

EXAMPLE 20

This example illustrates the preparation of a mPEG-PDO diblock copolymer according to formula I.

The procedure of Example 1 was repeated using 5 g of poly(ethylene glycol) monomethyl ether (Mw 2,000 Daltons), 2.08 g of 1,4-dioxane-2-one and 10.13 mg of stannous octoate at a region temperature of 100° C. to obtain a mPEG-PDO diblock copolymer(Mw 2,000–480 Daltons). The mPEG content of this copolymer was 81.0 wt %.

EXAMPLE 21

This example illustrates the preparation of a PDO-PEG-PDO triblock copolymer according to formula II.

The procedure of Example 1 was repeated using 5 g of poly(ethylene glycol)(Mw 3,400 Daltons), 0.6 g of 1,4-dioxane-2-one and 23.8 mg of stannous octoate at a reaction temperature of 80° C. to obtain a PDO-PEG-PDO triblock copolymer (Mw 200–3,400–200 Daltons). The PEG content of this copolymer was 89.0 wt %.

EXAMPLE 22

This example illustrates the solubilities of the copolymers of the present invention in various solvents.

The solubilities of the block polymers synthesized in Example 1 to 21 in dichloromethane, chloroform, acetic acid, acetone, and distilled water were measured and the results are shown in Table 1.

TABLE 1

Solubility of block copolymers

| Example No. | Dichloromethane | Chloroform | Acetic acid | Acetone | Water |
|---|---|---|---|---|---|
| 1 | ○ | ○ | ○ | ○ | Δ |
| 2 | ○ | ○ | ○ | ○ | X |
| 3 | ○ | ○ | ○ | ○ | X |
| 4 | ○ | ○ | ○ | ○ | X |
| 5 | ○ | ○ | ○ | ○ | X |
| 6 | ○ | ○ | ○ | ○ | ○ |
| 7 | ○ | ○ | ○ | ○ | X |
| 8 | ○ | ○ | ○ | ○ | X |
| 9 | ○ | ○ | ○ | ○ | X |
| 10 | ○ | ○ | ○ | ○ | X |
| 11 | ○ | ○ | ○ | ○ | X |
| 12 | ○ | ○ | ○ | ○ | X |
| 13 | ○ | ○ | ○ | ○ | X |
| 14 | ○ | ○ | ○ | ○ | X |
| 15 | ○ | ○ | ○ | ○ | X |
| 16 | ○ | ○ | X | X | X |
| 17 | ○ | ○ | ○ | ○ | ○ |
| 18 | X | X | X | X | X |
| 19 | X | X | X | X | X |
| 20 | ○ | ○ | ○ | ○ | ○[a] |
| 21 | ○ | ○ | ○ | ○ | ○[b] |

○ freely soluble, Δ soluble, X practically insoluble
[a]solubility of 1.8 g/mL, [b]solubility of 2.0 g/mL

EXAMPLE 23

This example illustrates the preparation of mPEG-PDO diblock copolymers microspheres.

An 0.85 g sample of the mPEG-PDO diblock copolymer (Mw 5,000–5,800 Daltons) synthesized in Example 4 was dissolved in 2 ml of dichloromethane and 0.15 g of ofloxacin was suspended therein. The suspension was added to a 1 wt % polyvinylalcohol aqueous solution and stirred at 1,200 rpm for 3 hours to obtain a microsphere solution. The microsphere solution obtained was freeze-dried to obtain microspheres having an average particle size of 10 μm and containing 14.6 wt % ofloxacin.

EXAMPLE 24

This example illustrates the preparation of mPEG-PDO diblock copolymer nanospheres.

An 0.85 g sample of the mPEG-PDO diblock copolymer (Mw 2,000–2,100 Daltons) synthesized in Example 3 and 0.15 g of pacitaxel were dissolved in 5 ml of acetone and 15 ml of distilled water, heated to 60° C. to obtain a clear solution which was then stirred at 600 rpm for 1 hour 15 ml of distilled water was added thereto and the solution was passed through a 0.8 mm membrane filter. The filtrate obtained was freeze-dried to obtain nanospheres having an average particle size of 0.45 μm and containing 13.6 wt % pacitaxel.

EXAMPLE 25

This example illustrates the preparation of a mPEG-PDO/PLA diblock copolymer micelle.

An 0.85 g sample of the mPEG-PDO/PLA diblock copolymer(Mw 2,000–710/1,120 Daltons) synthesized in Example 6 and 0.01 g of paclitaxel were dissolved in 0.2 ml of acetone and 2 ml of distilled water was added thereto to obtain a clear solution. The solution thus obtained was filtered and the filtrate was freeze-dried to obtain nanospheres having an average particle size of 0.45 μm and containing 13.6 wt % paclitaxel.

EXAMPLE 26

This example illustrates the preparation of PDO/PLA-PEG-PDO/PLA triblock copolymer microspheres.

An 0.80 g sample of the PDO/PLA-PEG-PDO/PLA triblock copolymer(Mw 1,290/1,710–3,400–1,290/1,710 Daltons) synthesized in Example 11 and 0.2 g of paclitaxel were dissolved in 2 ml of dichloromethane and microspheres having an average particle size of 48 μm and containing 19.3 wt % paclitaxel were prepared in accordance with the procedure of Example 16.

EXAMPLE 27

This example illustrates the preparation of PDO/PLA-PEG-PDO/PLA triblock copolymer microspheres.

A 2.40 g sample of the PDO/PLA-PEG-PDO/PLA triblock copolymer(Mw 1,290/1,710–3,400–1,290/1,710 Daltons) synthesized in Example 11 and 0.6 g of human growth hormone were dissolved in 10 ml of acetic acid and freeze-dried to obtain a powder. The powder thus obtained was pressed under a pressure of 2 ton/cm$^2$ to prepare a 1 mm×10 mm cylindrical piece. The cylindrical piece was added to 5 ml of phosphate buffer solution(10 M, pH 7.4) and the amount of the growth hormone released in the buffer solution was measured while shaking at 37° C. and 50 rpm. The results are shown in Table 2.

TABLE 2

Cumulative amount of drug released in buffer solution

| Time (days) | Drug released (%) |
|---|---|
| 1 | 12 |
| 3 | 27 |
| 5 | 39 |
| 7 | 48 |
| 9 | 53 |
| 11 | 58 |
| 13 | 61 |
| 15 | 66 |
| 17 | 69 |
| 19 | 72 |
| 21 | 75 |
| 23 | 78 |
| 25 | 81 |
| 27 | 84 |
| 29 | 87 |

EXAMPLE 28

The example illustrates the preparation of a PDO-PEG-PDO triblock gel.

An 0.80 g sample of the PDO-PEG-PDO triblock copolymer (Mw 3,640–3,400–3,640 Daltons) synthesized in Example 9 and 0.2 g of paclitaxel were dissolved in 3 ml of N-methylpyrrolidone to obtain a gel. The gel was then injected in water to form a polymeric implant containing paclitaxel.

EXAMPLE 29

An 0.80 g sample of the mPEG-PDO diblock copolymer (Mw 2,000–480 Daltons) synthesized in Example 20 and 0.2 g of paclitaxel were dissolved in 1 ml of acetonitrile to obtain a homogeneous solution and the resulting solution was added to 0.2% polyvinyl alcohol. However, polymeric micelles were not obtained due to the excessive solubility of the polymer in the aqueous solution. This indicates that mPEG-PDO diblock copolymers containing 81% by weight of mPEG are not suitable for preparing a drug containing micelle.

EXAMPLE 30

A 1.80 g of the PDO-PEG-PDO triblock copolymer(Mw 200–3,400–200 Daltons) synthesized in Example 21 and 0.2 g of porcine growth hormone were dissolved in 1 ml of distilled water and freeze-dried to obtain polymer particle containing the growth hormone. The polymer particles were added to distilled water to measure the rate of drug release, but the particles simply dissolved in water. This indicates that a PDO-PEG-PDO triblock copolymer containing 89% by weight of mPEG are not suitable for preparing a drug containing implant.

While the invention has been described with respect to the above specific embodiments, it should be recognized that various modifications and changes may be made to the invention by those skilled in the art which also fall within the scope of the invention as defined by the appended claims.

We claim:

1. A block copolymer comprising one or more poly (alkylene oxide) blocks and one or more blocks of a p-dioxanone homopolymer or copolymer, wherein:
   (a) the block copolymer has a solubility in an organic solvent of 33.3 to 1,000 mg/ml; and
   (b) the poly(alkylene oxide) blocks comprise between 25% to 80% by weight of the block copolymer.

2. The block of claim 1, wherein the poly(alkylene oxide) blocks comprises between 30 to 75% by weight of the block copolymer.

3. The block copolymer of claim 1 having an average molecular weight of between 625 to 2,000,000 Daltons.

4. The block copolymer of claim 1, wherein the total molecular weight of the poly(alkylene oxide) blocks is within range from 200 to 500,000 Daltons.

5. The block copolymer of claim 1, wherein the poly (alkylene oxide) is a member selected from the group consisting of poly(ethylene oxide), random copolymers of ethylene oxide and propylene oxide and block copolymers of poly(ethylene oxide) and poly(propylene oxide) and monoalkoxy-terminated derivatives thereof.

6. The block copolymer claim 1, wherein the p-dioxanone copolymer is a copolymer of 1,4-dioxane-2-one and a member selected from the group consisting of glycolic acid, lactic acid, and caprolactone.

7. The block copolymer of claim 6, wherein the p-dioxanone copolymer contains at least 5 mole percent of repeating units derived from 1,4-dioxane-2-one based on the total amount of monomers used in preparing said copolymer.

8. The block copolymer of claim 1, wherein the block copolymer is a diblock or triblock copolymer.

9. The block copolymer of claim 1 wherein said block copolymer is selected from the group consisting of RO—A—B—OH, RO—B—A—B—OR, RO—A—B—A—OR and RO—(A—B)$_n$—OR, wherein R is hydrogen, an alkyl or acyl group having 1~20 carbon atoms, n is an integer of 2 to 100; A is a hydrophillic poly(alkylene oxide) block selected from the group consisting of poly(ethylene oxide), random copolymers of ethylene oxide and propylene oxide and block copolymers of poly(ethylene oxide) and poly(propylene oxide); and B is a hydrophobic block selected from the group consisting of poly(p-dioxanone), a block or random copolymer of 1,4-dioxanone and at least one comonomer selected from the group consisting of lactic acid, glycolic acid and carprolactone.

10. The block copolymer claim 1, wherein the organic solvent is a member selected from the group consisting of methylene chloride, chloroform, ethanol, methanol, isopropanol, butanol, acetic acid, formic acid, ethyl acetate, methyl acetate, acetonitrile, acetone, 1,4-dioxane, N,N-dimethyl formamide, N,N-dimethyl acetamide, dimethyl sulfoxide, N-methylpyrrolidone, or a mixture thereof.

11. A bioactive agent delivery composition comprising the block copolymer of claim 1 and a bioactive agent encased therein.

12. The composition of claim 11, wherein the bioactive agent is a member selected from the group consisting of peptides or proteins, anti-cancer agents, antiphlogistic anodyme agents, anti-biotic agents, anti-bacterial agents, hormones, genes and vaccines.

13. The composition of claim 1, wherein the bioactive agent is selected from the group consisting of paclitaxel, cisplatin, carboplatin, doxorubicin, camtotecin, 5-fluorouracil, cytosine arabinoside, methotrexate, indomethacin, probiprofen, ketoprofen, piroxicam, diclofenac, cyclosporine, etraconazole, ketoconazole, tetracycline, minocycline, doxycycline, ofloxacin, ciprofloxacin, gentamicin, amphotericin B human growth hormone, pig growth hormone, bovine growth hormone, leukocyte increasing factors, erythrocyte increasing agent, osteogenetic protein, platelet sensitive agent, epithelial cell growth factor, brain growth factor, leuprorelin acetate, goserelin acetate, insulin, glucagon, octreotide, calcitonin, decapeptyl, follicle-stimulating hormone, interferon, testosterone, progesterone, estradiol, estrogen.

14. A drug formulation for subcutaneous implantation of intravenous injection comprising the composition of claim 11.

15. A drug formulation for subcutaneous implantation or intravenous injection comprising a bioactive agent delivery composition comprising a block copolymer comprising one or more poly(alkylene oxide) blocks and one or more blocks of a p-dioxanone homopolymer or copolymer, wherein:
   (a) the block copolymer is soluble in an organic solvent; and
   (b) the poly(alkylene oxide) blocks comprise between 25 to 85% by weight of the block copolymer;
and a bioactive agent encased therein, wherein said composition is in the form of a microsphere, microcapsule, film, strip, fiber, gel or solution.

16. A drug formation for subcutaneous implantation or intravenous injection comprising a bioactive agent delivery composition comprising a block copolymer comprising one or more poly(alkylene oxide) blocks and one or more blocks of a p-dioxanone homopolymer or copolymer, wherein:
   (a) the block copolymer is soluble in an organic solvent; and
   (b) the poly(alkylene oxide) blocks comprise between 25 to 80% by weight of the block copolymer;
and a bioactive agent encased therein, wherein said composition is in the form of a nanosphere, nanocapsule or polymeric micelle.

* * * * *